United States Patent [19]

Kulprathipanja

[11] 4,433,195
[45] Feb. 21, 1984

[54] SEPARATION OF TRANS- AND CIS-OLEFINS

[75] Inventor: Santi Kulprathipanja, Hoffman Estates, Ill.

[73] Assignee: UOP Inc., Des Plaines, Ill.

[21] Appl. No.: 471,397

[22] Filed: Mar. 2, 1983

[51] Int. Cl.$^3$ ............................................... C07C 7/12
[52] U.S. Cl. ..................................... 585/820; 585/825; 585/829
[58] Field of Search .................... 585/820, 825, 829

[56] References Cited

U.S. PATENT DOCUMENTS

| | | | |
|---|---|---|---|
| 2,850,549 | 9/1958 | Ray | 260/677 |
| 3,524,895 | 8/1970 | Chen et al. | 260/677 |
| 4,061,724 | 12/1977 | Grose et al. | 423/335 |
| 4,104,294 | 8/1978 | Grose et al. | 260/448 |

Primary Examiner—Curtis R. Davis
Attorney, Agent, or Firm—James R. Hoatson, Jr.; Louis A. Morris; William H. Page, II

[57] ABSTRACT

A process for the separation of a trans-olefin from a cis-olefin. A mixture of the trans- and cis-olefins is contacted with an adsorbent comprising silicalite which is selective for the trans-olefin. The process is particularly suitable for the separation of trans-2-butene from cis-2-butene.

22 Claims, 4 Drawing Figures

SEPARATION OF TRANS- AND CIS-OLEFINS

BACKGROUND OF THE INVENTION

Cis- and trans- compounds are geometric isomers. The phenomenon of geometric isomerism is a general one and can be encountered in any class of compounds that contain carbon-carbon double bonds. The cis- differ from trans- only in the way the atoms are oriented in space. One example of a geometric isomers are cis-2-butene and trans-2-butene. Both cis- and trans-2-butene contain one carbon-carbon double bond. The only difference is the orientation of each methyl group on the two carbon-carbon double bond. The two methyl groups will be on the same side of the double bond for cis-2-butene; they will be on the opposite sides for trans-2-butene.

It is known to the art that the separation of geometric isomers can be carried out by either crystallization, precipitation, fractional distillation, solvent extraction and adsorption. Adsorption technique is getting more attention recently because high purity and high efficiency can be obtained from the process. High purity separation of geometric isomers by fractionation is often difficult because of the closeness of the boiling point of the particular isomers, e.g., trans-2-butene boils at 1° C. and cis-2-butene at 4° C.

It is also well known to use aluminosilicates (zeolites) as the adsorbents in the above mentioned adsorption technique. U.S. Pat. No. 2,850,549 to Ray teaches the use of chabazite as an adsorbent in a method for the separation of the components of a pair of cis- and trans-isomers containing the same number of carbon atoms per molecule such as cis- and trans-isomers of straight chain $C_4$, $C_5$ and $C_6$ olefins. U.S. Pat. No. 3,524,895 to Chen et al discloses the use of various aluminosilicates, particularly erionite, for a similar separation method.

Notwithstanding the above patents, however, no commercial adsorption process in the geometric isomers separation exists at the moment. The reason could be the reactivity between zeolites with olefinic compounds. In order to maintain the long term stability of the absorbent, an inert adsorbent is needed for the separation of geometric olefin isomers.

A new composition of matter referred to as "silicalite," has recently been developed and patented (see U.S. Pat. Nos. 4,061,724 and 4,104,294 to Gross et al). Silicalite is said by its inventors to have utility in separating organics from water.

I have made the discovery that silicalite is able to effect the separation of a trans-olefin from a cis-olefin with substantially complete elimination of the aforementioned undesired side effects of dimerization and polymerization.

SUMMARY OF THE INVENTION

In one embodiment, the present invention is a process for separating a trans-olefin from a feed containing a trans-olefin and a cis-olefin comprising contacting the feed at adsorption conditions with an adsorbent comprising silicalite to effect selective adsorption of the trans-olefin, and removing the cis-olefin from contact with the trans-olefin containing adsorbent.

In another embodiment, the present invention comprises a process for separating a trans-olefin from a feed containing a trans-olefin and a cis-olefin using an adsorbent comprising silicalite, which process comprises the step of: (a) maintaining net fluid flow through a column of the absorbent in a single direction, which column contains at least three separate and serially interconnected zones; (b) maintaining an adsorption zone defined by the feed inlet and raffinate outlet as a downstream boundary; (c) maintaining a purification zone defined by an extract outlet and the feed inlet as a downstream boundary; (d) maintaining a desorption zone defined by a desorbent inlet and the extract outlet as a downstream boundary; (e) passing the feed into the adsorption zone at adsorption conditions and adsorbing the trans-olefin and withdrawing a raffinate stream containing the cis-olefin; (f) passing a desorbent material into the desorption zone at desorption conditions and displacing the trans-olefin from the adsorbent; (g) withdrawing an extract stream comprising the trans-olefin and desorbent from the desorption zone; and, (h) periodically advancing through the column of adsorbent in a downstream direction with respect to fluid flow, the feed inlet, raffinate outlet, desorbent inlet, and extract outlet to shift zones through the adsorbent.

Other embodiments of the invention encompass details about feed mixtures, adsorbents, desorbent materials and operating conditions, all of which are hereinafter disclosed in the following discussion of each of the facets of the present invention.

DESCRIPTION OF THE INVENTION

Figure 1:
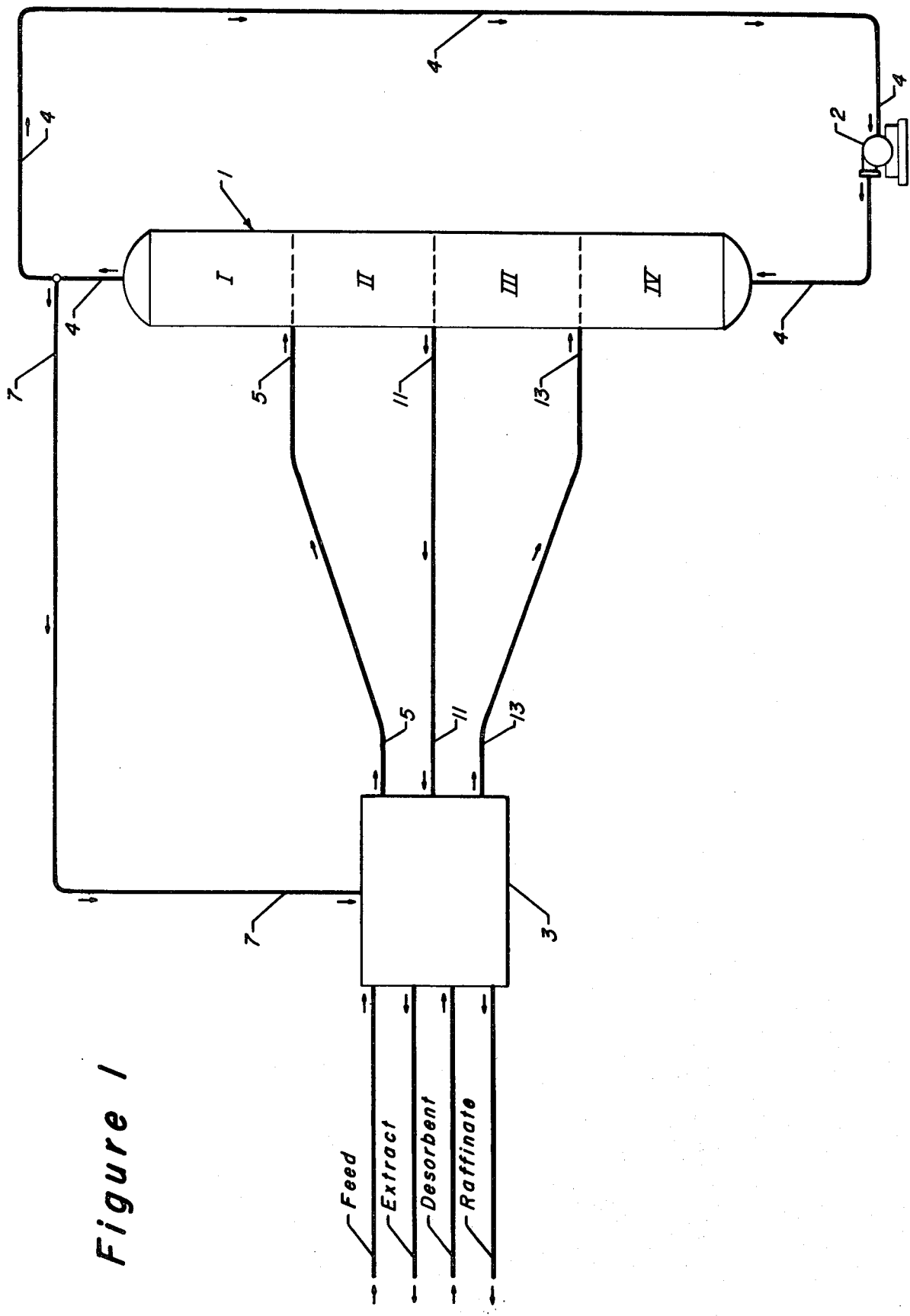
FIG. 1 represents, in schematic form, the embodiment of the present invention incorporating a simulated moving bed, hereinafter described, including adsorption column 1, manifold system 3 and various interconnecting lines.

At the outset the definitions of various terms used throughout the specification will be useful in making clear the operation, objects and advantages of the present process.

A "feed mixture" is a mixture containing one or more extract components and one or more raffinate components to be separated by the process. The term "feed stream" indicates a stream of a feed mixture which passes to the adsorbent used in the process.

An "extract component" is a component that is more selectively adsorbed by the adsorbent while a "raffinate component" is a component that is less selectively adsorbed. In this process, trans-olefin is an extract component and cis-olefin is a raffinate component. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream, and preferably at least a portion of the raffinate stream, from the separation process are passed to separation means, typically fractionators or evaporators, where at least a portion of desorbent material is separated to produce an extract product and a raffinate product. The term "extract product" and "raffinate product" mean products produced by the process containing, respectively, an extract component and a raffinate component in higher concentrations than those found in the extract stream and the raffinate stream. Although it is possible by the process of this invention to produce a high purity trans-olefin product at high recoveries, it will be appreciated that an extract component is never completely adsorbed by the adsorbent, nor is a raffinate component completely nonadsorbed by the adsorbent. Therefore, varying amounts of a raffinate component can appear in the extract stream and, likewise, varying amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of trans-olefin to that of less selectively adsorbed cis-olefin will be lowest in the raffinate stream, next highest in the feed mixture, and the highest in the extract stream. Likewise, the ratio of the concentration of less selectively adsorbed cis-olefin to that of a more selectively adsorbed trans-olefin will be highest in the raffinate stream, next highest in the feed mixture, and the lowest in the extract stream.

The term "selective pore volume" of the adsorbent is defined as the volume of the adsorbent which selectively adsorbs an extract component from the feed mixture. The term "non-selective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent. When adsorbent "passes" into an operational zone (hereinafter defined and described) employed in one embodiment of this process, its non-selective void volume, together with its selective pore volume, carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it, in most instances, comprises less selectively retained feed components. The selective pore volume of an adsorbent can in certain instances adsorb portions of raffinate material from the fluid surrounding the adsorbent, since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

Feed stocks which can be utilized in the process of this invention can be derived from any of the refinery processes known to the art. Specifically, the feed stocks include trans- and cis-mono-olefinic hydrocarbons such as trans-butene-2 and cis-butene-2. Other materials can be present in the feed stock such as large quantities of paraffinic or naphthene substances and in some instances low concentrations of aromatic hydrocarbons and other contaminant substances such as the combined sulfur nitrogen compounds. It is preferred, however, to substantially reduce the quantity of components which would contribute to the deactivation of the adsorbent by blocking off the adsorptive site passageways to feed stock components.

Specific feed stocks which can be utilized in the process of this invention may also include amounts of materials other than geometric isomers such as butene-1, isobutylene, and iso-butane or normal butane.

Desorbent materials used in various prior art adsorptive separation processes vary depending upon such factors as the type of operation employed. In the swing bed system, in which the selectively adsorbed feed component is removed from the adsorbent by a purge stream, desorbent selection is not as critical and desorbent material comprising gaseous hydrocarbons such as methane, ethane, etc., or other types of gases such as nitrogen or hydrogen, may be used at elevated temperatures or reduced pressures or both to effectively purge the adsorbed feed component from the adsorbent. However, in adsorptive separation processes which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high nor would the desorbent material be available for reuse in the process. It is therefore contemplated that any desorbent material used in this process will preferably have a substantially different average boiling point than that of the feed mixture to allow separation of at least a portion of desorbent material from feed components in the extract and raffinate streams by simple fractional distillation, thereby permitting reuse of desorbent material in the process. The term "substantially different" as used herein shall mean that the difference between the average boiling points between the desorbent material and the feed mixture shall be least about 5° C. The boiling range of the desorbent material may be higher or lower than that of the feed mixture. Finally, desorbent materials should also be materials which are readily available and therefore reasonable in cost. In the preferred isothermal, isobaric, liquid-phase operation of the process of this invention, it has been found that desorbent material comprising a normal hydrocarbon meet these requirements and is particularly effective. It is usually advantageous to mix the desorbent with a non-adsorbed diluent such as a non-normal hydrocarbon. For separating cis- from trans-butene-2, pentene-1 is a particularly effective desorbent particularly when mixed with isopentane in a 50/50 blend.

The prior art has recognized that certain characteristics of adsorbents are highly desirable, if not absolutely necessary, to the successful operation of a selective adsorption process. Such characteristics are equally important to this process. Among such characteristics are: adsorptive capacity for some volume of an extract component per volume of adsorbent; the selective adsorption of an extract component with respect to a raffinate component and the desorbent material; and sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component, the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions. Relative selectivity is shown in Equation 1, below:

Equation 1
$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases, respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0, there is no preferential adsorption of one component by the adsorbent with respect to the other; they are both adsorbed (or non-adsorbed) to about the same degree with respect to each other. As the (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1.0, it is preferred that such selectivity be greater than 2.0. Like relative volatility, the higher the selectivity, the easier the separation is to perform. Higher selectivities permit a smaller amount of adsorbent to be used. The third important characteristic is the rate of exchange of the extract component of the feed mixture material, or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent, is injected for a duration of several minutes. Desorbent flow is resumed, and the tracer and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, adsorbent performance can be rated in terms of void volume, retention volume for an extract, or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (B) for an extract component with respect to a raffinate component, may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width, the faster the desorption rate. The desorption rate can be characterized by the distance between the center of the tracer peak envelope and the disappearance of an extract component which has just been desorbed. This distance is again the volume of desorbent pumped during this time interval.

The adsorbent to be used in the process of this invention comprises silicalite. As previously mentioned, silicalite is a hydrophobic crystalline silica molecular sieve. Due to its aluminum-free structure, silicalite does not show ion-exchange behavior, and is hydrophobic and organophilic. Silicalite thus comprises a molecular sieve, but not a zeolite. Silicalite is uniquely suitable for the separation process of this invention for the presumed reason that its pores are of a size and shape that enable the silicalite to function as a molecular sieve, i.e. accept the molecules of normal $C_4$ hydrocarbons into its channels or internal structure, while rejecting the molecules of isobutylene. A detailed discussion of silicalite may be found in the article "Silicalite, A New Hydrophobic Crystalline Silica Molecular Sieve" ; *Nature*, Vol. 271, 9 Feb. 1978, incorporated herein by reference.

The adsorbent may be employed in the form of a dense compact fixed bed which is alternatively contacted with the feed mixture and desorbent materials. In the simplest embodiment of the invention, the adsorbent is employed in the form of a single static bed in which case the process is only semi-continuous. In another embodiment, a set of two or more static beds may be employed in fixed bed contacting with appropriate valving so that the feed mixture is passed through one or more adsorbent beds, while the desorbent materials can be passed through one or more of the other beds in the set. The flow of feed mixture and desorbent materials may be either up or down through the desorbent. Any of the conventional apparatus employed in static bed fluid-solid contacting may be used. The particles of silicalite adsorbent will preferably have a particle size range of about 16–60 mesh (Standard U.S. Mesh).

Silicalite itself is a fine powder and therefore must be bound to obtain the above particle size. Alumina and/or silica, including clay, are acceptable binders, although a fluid permeable organic polymer should be at least as effective particularly polystyrenedivinylbenzene. The organic polymer offers the further advantage of greater resistance to dissolution of the adsorbent.

Countercurrent moving bed or simulated moving bed counter-current flow system, however, have a much greater separation efficiency than fixed adsorbent bed systems and are therefore preferred for use in this separation process. In the moving bed or simulated moving bed processes, the adsorption and desorption operations are continuously taking place which allows both continuous production of an extract and a raffinate stream and the continual use of feed and desorbent streams. One preferred embodiment of this process utilizes what is known in the art as the simulated moving bed countercurrent flow system. The operating principles and sequence of such a flow system are described in U.S. Pat. No. 2,985,589 incorporated herein by reference thereto. In such a system, it is the progressive movement of multiple liquid access points down an adsorbent chamber that simulates the upward movement of adsorbent contained in the chamber. Only four of the access lines are active at any one time: the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of the process, it is generally necessary that three separate operational zones be present in order for the process to take place although in some instances an optional fourth zone may be used. There is a net positive fluid flow through all portions of the column in the same direction, although the composition and rate of the fluid will, of course, vary from point to point. With reference to FIG. 1, zones I, II, III and IV are shown as well as manifold system 3, pump 2, which maintains the net positive fluid flow, and line 4 associated with pump 2. Also shown and identified are the inlet and outlet lines to the process which enter or leave via manifold system 3.

The adsorption zone, zone I, is defined as the adsorbent located between the feed inlet stream 5 and the raffinate outlet stream 7. In this zone, the feedstock contacts the adsorbent, an extract component is adsorbed, and a raffinate stream is withdrawn. Since the general flow through zone I is from the feed stream which passes into the zone to the raffinate stream which passes out of the zone, the flow in this zone is considered to be in a downstream direction when proceeding from the feed inlet to the raffinate outlet streams.

Immediately upstream with respect to fluid flow in zone I is the purification zone, zone II. The purification zone is defined as the adsorbent between the extract outlet stream and the feed inlet stream 5. The basic operations taking place in zone II are the displacement from the non-selective void volume of the adsorbent of any raffinate material carried into zone II by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone III into zone II at zone II's upstream boundary, the extract outlet stream, to effect the displacement of raffinate material. The flow of material in zone II is in a downstream direction from the extract outlet stream to the feed inlet stream.

Immediately upstream of zone II with respect to the fluid flowing in zone II is the desorption zone, or zone III. The desorption zone is defined as the adsorbent between the desorbent inlet 13 and the extract outlet stream 11. The function of the desorption zone is to allow a desorbent material which passes into this zone to displace the extract component which was adsorbed upon the adsorbent during a previous contact with feed in zone I in a prior cycle of operation. The flow of fluid in zone III is essentially in the same direction as that of zones I and II.

In some instances, an optional buffer zone, zone IV, may be utilized. This zone, defined as the adsorbent between the raffinate outlet stream 7 and the desorbent inlet stream 13, if used, is located immediately upstream with respect to the fluid flow to zone III. Zone IV would be utilized to conserve the amount of desorbent utilized in the desorption step since a portion of the raffinate stream which is removed from zone I can be passed into zone IV to displace desorbent material present in that zone out of that zone into the desorption zone. Zone IV will contain enough adsorbent so that raffinate material present in the raffinate stream passing out of zone I and into zone IV can be prevented from passing into zone III, thereby contaminating the extract stream removed from zone IV. In the instances in which the fourth operational zone is not utilized, the raffinate stream passed from zone I to zone IV must be carefully monitored in order that the flow directly from zone I to zone III can be stopped when there is an appreciable quantity of raffinate material present in the raffinate stream passing from zone I into zone III so that the extract outlet stream is not contaminated.

A cyclic advancement of the input and output streams through the fixed bed of adsorbent can be accomplished by utilizing a manifold system 3 in which the valves in the manifold are operated in a sequential manner to effect the shifting of the input and output streams, thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically, rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone of all of them. Since it is not required that the adsorbent be located in a single column, the use of multiple chambers or a series of columns is within the scope of the invention.

It is not necessary that all of the input or output streams by simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternatively and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent stream which can be reused in the process and a raffinate product containing a reduced concentration of desorbent material. The separation means will typically be a fractionation column or an evaporator, the design and operation of either being well known to the separation are.

Reference can be made to D. B. Broughton U.S. Pat. No. 2,985,589, and to a paper entitled "Continuous Adsorptive Processing—A new Separation Technique" by D. B. Broughton presented at the 34th Annual Meeting of the Society of Chemical Engineers at Tokyo, Japan, on Apr. 2, 1969 (both of which are incorporated herein by reference), for further explanation of the simulated moving bed countercurrent process flow scheme.

Although both liquid and vapor phase operations can be used in many adsorptive separation processes, liquid-phase operation is required for this process because of the lower temperature requirements and because of the higher yields of extract product that can be obtained with liquid-phase operation over those obtained with vapor-phase operation. Adsorption conditions will include a temperature range of from about 20° to about 200° C. with about 20° to about 100° C. being more preferred and a pressure range of from about atmospheric to about 500 psig with from about atmospheric to about 25 psig being more preferred to insure liquid phase. Desorption conditions will include the same range of temperatures and pressures as used for adsorption conditions.

The size of the units which can utilize the process of this invention can vary anywhere from those of pilot plant scale (see for example U.S. Pat. No. 3,706,812) to those of commercial scale and can range in flow rates from as little as a few cc an hour up to many thousands of gallons per hour.

The following examples are presented to illustrate the process of this invention. The examples are not intended to unduly restrict the scope and spirit of the claims attached hereto.

EXAMPLE I

In this example the above described pulse test apparatus was used to test the ability of clay bound silicalite to separate trans-butene-2 from a mixture of 5% isobutylene and 10% cis-and trans-butene-2 in desorbent at 60° C. with the desorbent comprising a 50:50 mixture of pentene-1 and isopentane. The isopentane served as a diluent to allow a more clear resolution of the elution curves.

Figure 2:
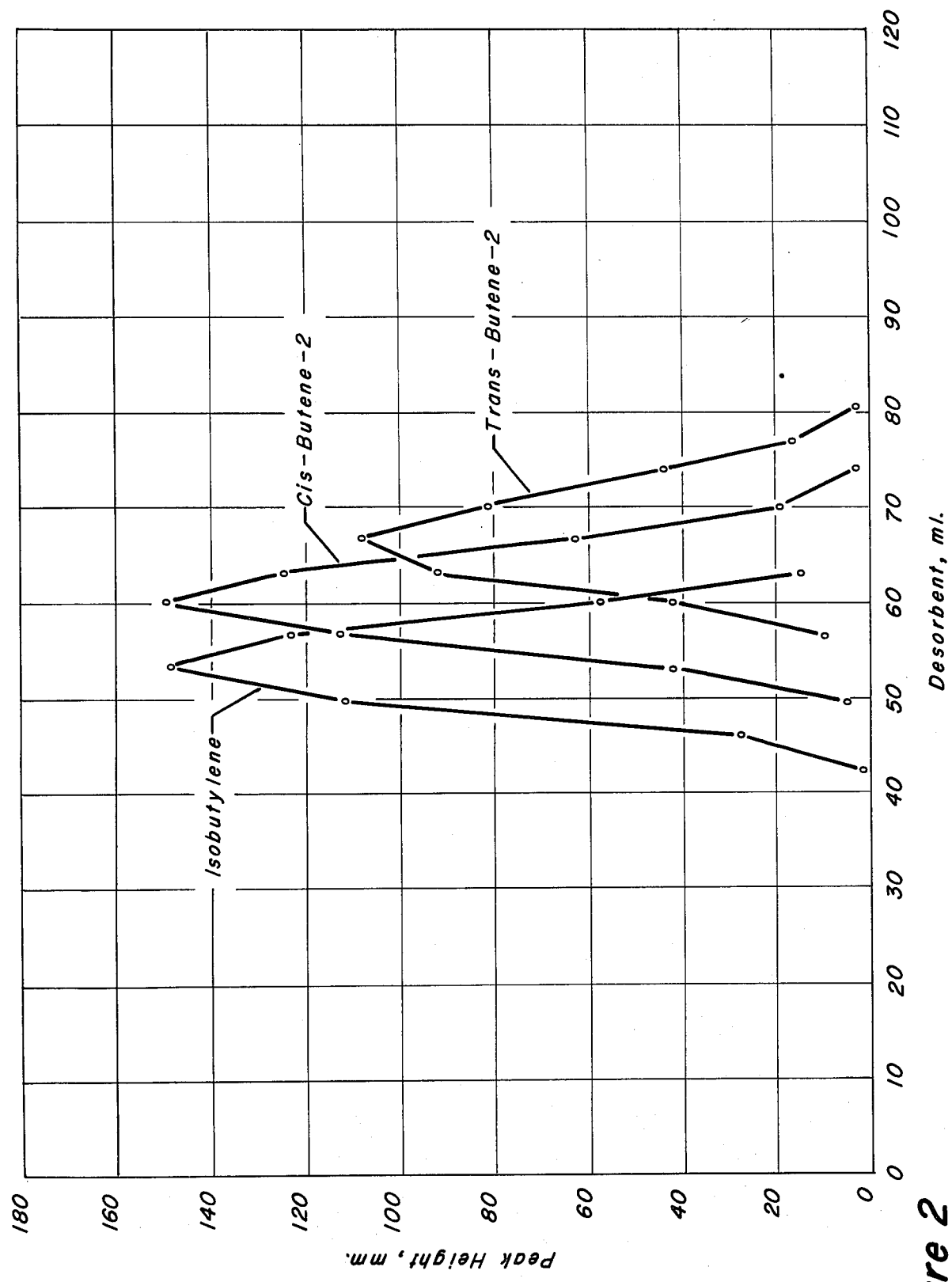
FIGS. 2, 3, and 4 comprise graphical representations of data obtained for the following examples.

The results are shown in the elution curves in FIG. 2. The separation of trans-butene-2 from cis-butene-2 was well pronounced. Also shown was that the silicalite would also reject the isobutylene into the raffinate. The selectivity of the adsorbent for the trans-in relation to the cis-isomer was calculated from the curves to be 1.96.

EXAMPLE II

Figure 3:
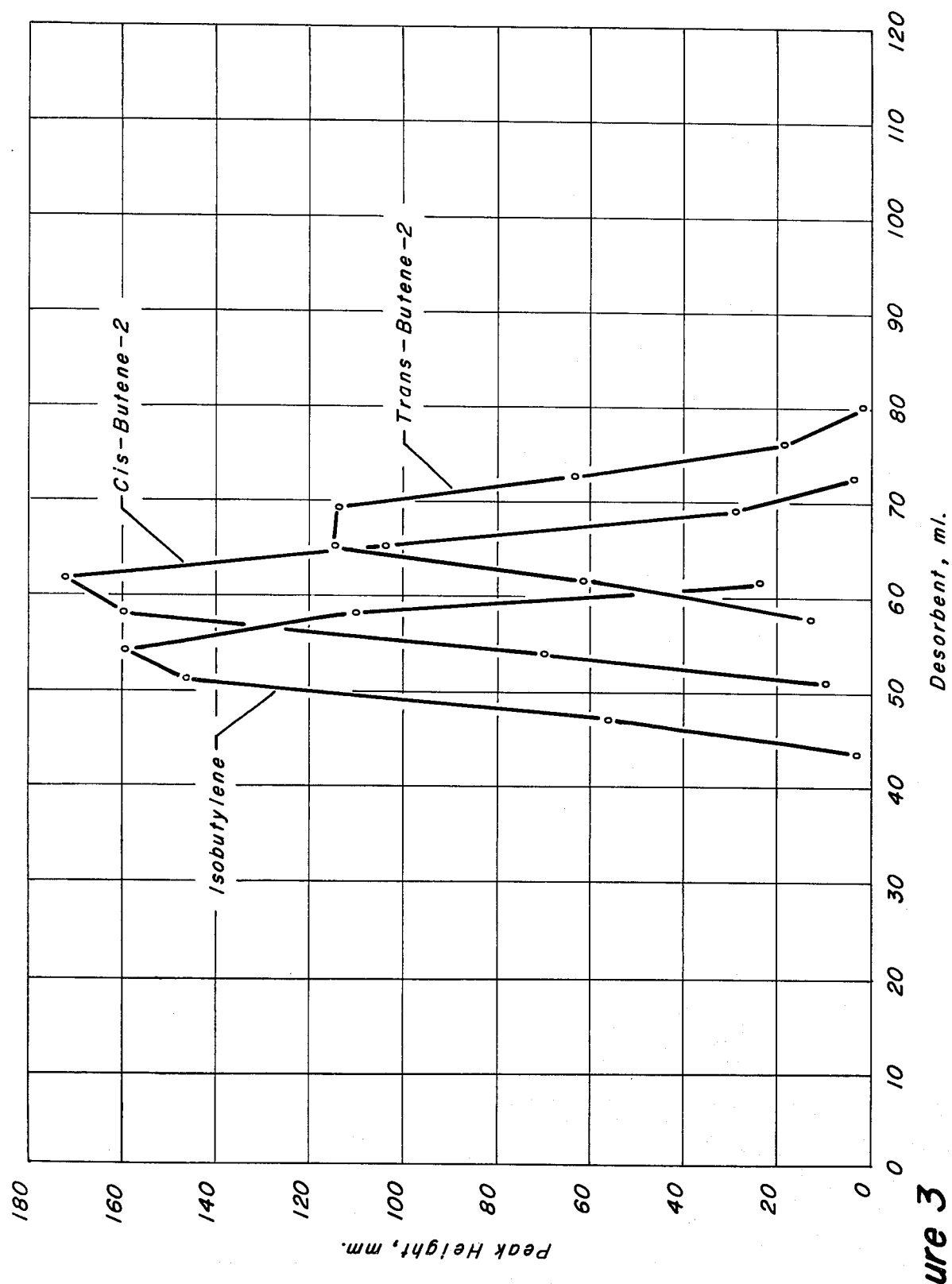

In this example the same separation as in Example I was effected with the same feed stream, desorbent and conditions as in Example I, but with the silicalite in this instance bound with alumina. FIG. 3 presents the pulse test data in the form of elution curves.

The desired separation was again achieved with a selectivity of trans- to cis-butene-2 of 2.00.

Example III

Figure 4:
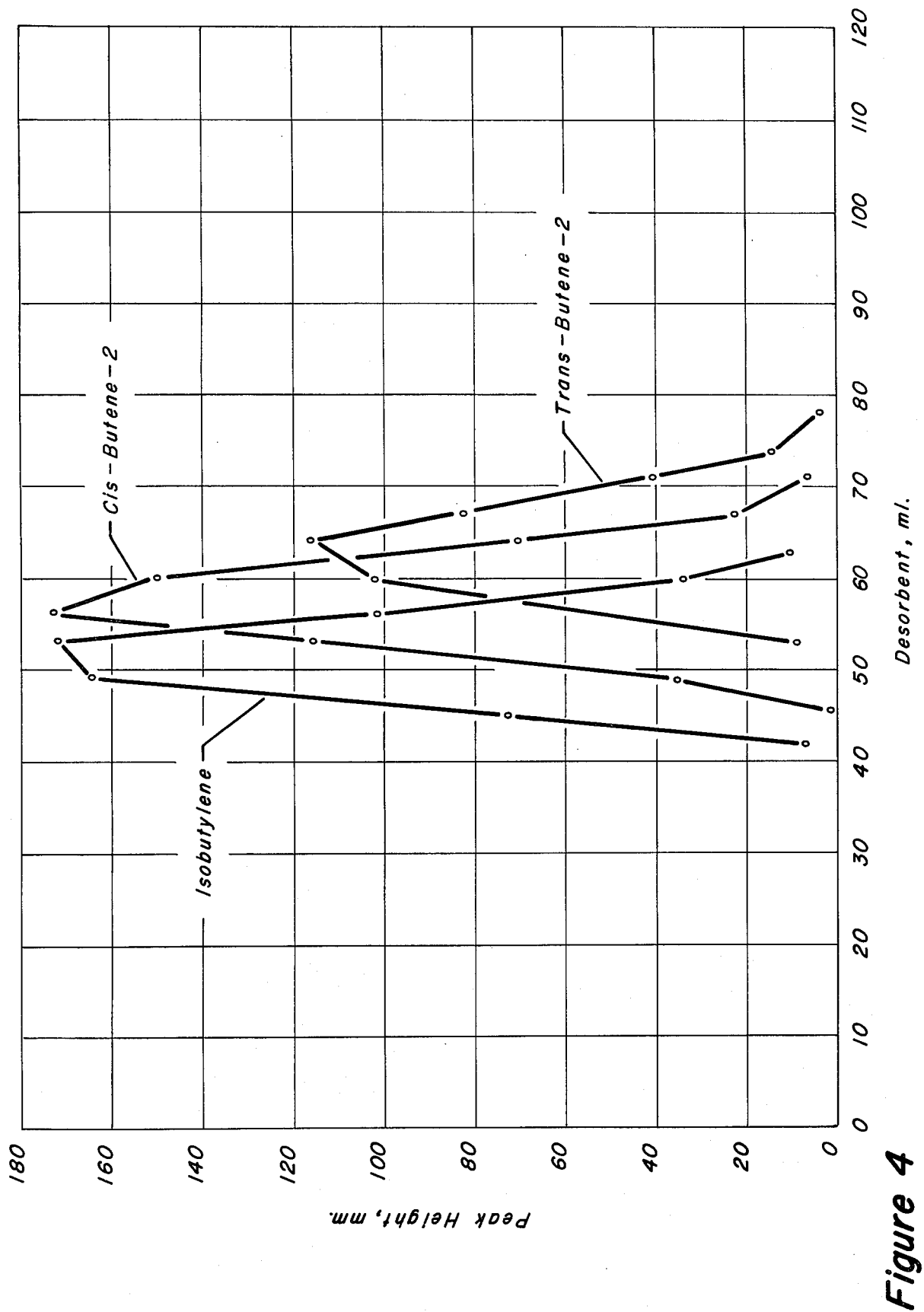

In this example Examples I and II were repeated except that the silicalite was silica bound. FIG. 4 presents pulse test data in the form of elution curves.

The desired separation was still again achieved with a selectivity of trans- to cis-butene-2 of 2.15.

In all of the above tests minimum chemical interaction between the olefins and adsorbent was observed, particularly with respect to dimerization of the olefins.

The invention claimed is:

1. A process for separating a trans-olefin from a feed containing a trans-olefin and a cis-olefin, comprising contacting said feed at adsorption conditions with an adsorbent comprising silicalite to effect selective adsorption of said trans-olefin and removing said cis-olefin from contact with said trans-olefin containing adsorbent.

2. The process of claim 1 wherein said adsorption conditions include a temperature within the range of from about 20° C. to about 200° C. and a pressure sufficient to maintain liquid phase.

3. The process of claim 1 wherein said adsorbent is regenerated by displacing said adsorbed trans-olefin with a desorbent material at desorption conditions.

4. The process of claim 3 wherein said desorption conditions include a temperature range within the range of from about 20° C. to about 200° C. and a pressure sufficient to maintain liquid phase.

5. The process of claim 3 wherein said desorbent material comprises a normal hydrocarbon.

6. The process of claim 3 wherein said olefins comprise trans-2-butene and cis-2-butene.

7. The process of claim 6 wherein said desorbent material comprises 1-pentene.

8. The process of claim 1 wherein said adsorbent comprises silicalite bound with alumina.

9. The process of claim 1 wherein said adsorbent comprises silicalite bound with a fluid permeable organic polymer.

10. The process of claim 1 wherein said adsorbent comprises silicalite bound with clay.

11. The process of claim 1 wherein said adsorbent comprises silicalite bound with silica.

12. A process for separating a trans-olefin containing a trans-olefin and a cis-olefin using an adsorbent comprising silicalite, which process comprises the steps of:
   (a) maintaining net fluid flow through a column of said adsorbent in a single direction, which column contains at least three separate and serially interconnected zones;
   (b) maintaining an adsorption zone defined by the feed inlet and raffinate outlet as a downstream boundary;
   (c) maintaining a purification zone defined by an extract outlet and said feed inlet as a downstream boundary;
   (d) maintaining a desorption zone defined by a desorbent inlet and said extract outlet as a downstream boundary;
   (e) passing said feed into said adsorption zone at adsorption conditions and adsorbing said trans-olefin and withdrawing a raffinate stream containing said cis-olefin;
   (f) passing a desorbent material into said desorption zone at desorption conditions and displacing said trans-olefin from said adsorbent;
   (g) withdrawing an extract stream comprising said trans-olefin and desorbent from said desorption zone; and,
   (h) periodically advancing through said column of adsorbent in a downstream direction with respect to fluid flow said feed inlet, raffinate outlet, desorbent inlet, and extract outlet to shift zones through said adsorbent.

13. The process of claim 12 wherein said raffinate stream is passed to a separation means wherein said desorbent is removed from said stream to produce substantially pure trans-olefin product.

14. The process of claim 13 wherein a buffer zone is maintained immediately upstream from said desorption zone, said buffer zone defined as the adsorbent located between the desorbent inlet in a downstream boundary of said buffer zone and a raffinate outlet at an upstream boundary of said buffer zone.

15. The process of claim 12 wherein said adsorption and desorption conditions include a temperature within the range of from about 20° C. to about 200° C. and a pressure sufficient to maintain liquid phase.

16. The process of claim 12 wherein said desorbent material comprises a normal hydrocarbon.

17. The process of claim 12 wherein said olefins comprise trans-2-butene and cis-2-butene.

18. The process of claim 17 wherein said desorbent material comprises 1-pentene.

19. The process of claim 12 wherein said adsorbent comprises silicalite bound with alumina.

20. The process of claim 12 wherein said adsorbent comprises silicalite bound with a fluid permeable organic polymer.

21. The process of claim 12 wherein said adsorbent comprises silicalite bound with silica.

22. The process of claim 12 wherein said adsorbent comprises silicalite bound with clay.

* * * * *